(12) United States Patent
Hoctor et al.

(10) Patent No.: US 9,759,690 B2
(45) Date of Patent: Sep. 12, 2017

(54) METHOD AND SYSTEM FOR NONDESTRUCTIVE ULTRASOUND TESTING

(75) Inventors: Ralph Thomas Hoctor, Saratoga Springs, NY (US); Stephen Eric Zingelewicz, Scotia, NY (US)

(73) Assignee: General Electric Company, Niskayuna, NY (US)

( * ) Notice: Subject to any disclaimer, the term of this patent is extended or adjusted under 35 U.S.C. 154(b) by 1940 days.

(21) Appl. No.: 13/033,896

(22) Filed: Feb. 24, 2011

(65) Prior Publication Data

US 2012/0216617 A1    Aug. 30, 2012

(51) Int. Cl.
*G01N 29/26* (2006.01)
*G01N 29/06* (2006.01)

(52) U.S. Cl.
CPC ....... *G01N 29/262* (2013.01); *G01N 29/0654* (2013.01)

(58) Field of Classification Search
CPC ......................... G01N 29/262; G01N 29/0654
USPC ............... 73/602, 624–626, 628, 633, 641
See application file for complete search history.

(56) References Cited

U.S. PATENT DOCUMENTS 4,497,210 A * 2/1985 Uchida et al. ................. 73/602
5,465,722 A   11/1995 Fort et al.
5,549,002 A * 8/1996 Howard et al. ................ 73/602
5,951,479 A   9/1999 Holm et al.
6,048,315 A   4/2000 Chiao et al.
6,551,246 B1  4/2003 Ustuner et al.
7,540,842 B2  6/2009 Napolitano et al.

OTHER PUBLICATIONS

Definition of angle—Merriam-Webster dictionary, downloaded Feb. 10, 2014.*
Jeremy A. Johnson; Mustafa Karaman; Butrus T. Khuri-Yakub; Coherent-Array Imaging Using Phased Subarrays. Part I: Basic Principles; IEEE Transactions on Ultrasonics, Ferroelectrics, and Frequency Control, vol. 52, No. 1, Jan. 2005.

* cited by examiner

*Primary Examiner* — Laura Martin
*Assistant Examiner* — Rose M Miller
(74) *Attorney, Agent, or Firm* — Pabitra K. Chakrabarti (57) ABSTRACT

Methods, systems and computer program products for nondestructive ultrasound imaging are provided. An example method defines a plurality of subarrays, each comprising a plurality of ultrasound transducer elements. The method transmits a plurality of ultrasound beams from each of the plurality of subarrays, each ultrasound beam being transmitted at a preset beamsteering angle. Subsequent to each transmit, the method receives, at the array, a plurality of ultrasound reflections corresponding to the plurality of ultrasound beams. For each point to be imaged, the method selects one set of received element data for each of the plurality of subarrays. The selected set of element data corresponds to an ultrasound beam having a focal point closest to the point to be imaged. Finally, the method reconstructs a point to be imaged based on the selected received element data, and constructs an ultrasound image by repeating this process for each point to be imaged.

24 Claims, 7 Drawing Sheets

METHOD AND SYSTEM FOR NONDESTRUCTIVE ULTRASOUND TESTING

BACKGROUND

Embodiments presented herein relate generally to ultrasound imaging systems, and more particularly to nondestructive evaluation using ultrasound imaging.

Ultrasound imaging is widely used for nondestructive testing of inaccessible portions of installed equipment. In nondestructive ultrasound testing, short ultrasonic pulses with frequencies between 0.1 and 15 MHz are launched into materials to detect internal flaws or to characterize materials. Nondestructive ultrasound testing is also commonly used to determine the thickness of the test object, for instance, to monitor pipework corrosion. Nondestructive ultrasound testing is often performed on steel and other metals and alloys. In some applications, nondestructive ultrasound testing may also be used on concrete, wood and composites.

In nondestructive ultrasound testing, uniform focus in the image is desirable. Uniform focus allows all points in the image to be evaluated for potential defects at the same time without adjustment of the nondestructive ultrasound tester. In medical imaging, the standard approach to achieving uniform focus is to use multiple transmit focal zones with dynamic receive focusing. However, such an approach typically does not yield sharp focus to enable multiple focal zones in the standard 16-element nondestructive ultrasound tester because of the large depth-of-focus of such a small array. Known portable instruments are generally confocal and only very weakly focused, even at the focal point.

One known technique to address this uniform focus problem includes synthetic focusing, such as Total Focus Method (TFM). In this approach, typically each array element is used to transmit separately with the entire array being used for receive, and image points are formed as a linear combination of the measured data, in such a way as to produce an image that is focused in both transmit and receive at every pixel. However, TFM generates a large amount of received ultrasound measurement data and subsequently requires a long image reconstruction time. Further, TFM may not penetrate deep into the object under test, since ultrasound transmissions are made with a single element. Another known technique, known as Synthetic Transmit Aperture (STA) addresses the problem of penetration by using subarrays for formation and transmission of ultrasound beams. In contrast to TFM, STA produces an image that is receive focused at every point, and only approximately transmit focused at every point. However, because STA was intended for use in medical imaging and required immunity to source motion, STA uses several transmissions to form each of a group of A-lines, which are then scan-converted to form an image. Thus, for an array with a relatively small number of elements, STA generates even more ultrasound measurement data than TFM.

Therefore, there is a need for an improved ultrasound imaging system for non-destructive testing that produces high resolution images, at high frame rates, and has lower computational requirement in addition to lower data transport and storage requirement.

BRIEF DESCRIPTION

The above and other drawbacks/deficiencies may be overcome or alleviated by embodiments of nondestructive ultrasound imaging presented herein. According to one embodiment, a method defines a plurality of subarrays. Each of the plurality of subarrays comprises a plurality of ultrasound transducer elements. The method then transmits a plurality of ultrasound beams from each of the plurality of subarrays. Each of the plurality of ultrasound beams is transmitted at a preset beamsteering angle. Subsequent to each such transmit, the method receives, at the array, a plurality of ultrasound reflections corresponding to the plurality of ultrasound beams. For each point to be imaged, the method selects one set of received element data for each of the plurality of subarrays. The selected set of element data corresponds to an ultrasound beam having a focal point closest to the point to be imaged. Finally, the method reconstructs a point to be imaged based on the selected received element data, and constructs an ultrasound image by repeating this process for each of a plurality of points to be imaged.

According to another embodiment, a method defines a plurality of subarrays. Each of the plurality of subarrays comprises a plurality of ultrasound transducer elements. The method then transmits a plurality of ultrasound beams from each of the plurality of subarrays. Each of the plurality of ultrasound beams is transmitted at a preset beamsteering angle. Subsequent to each such transmit, the method receives, at the array, a plurality of ultrasound reflections corresponding to the plurality of ultrasound beams, and converts the ultrasound reflections into corresponding ultrasound measurements. The method then processes the ultrasound measurements from each subarray by forming a complete complex image per subarray from at least some of the subarrays. Finally, the method combines said complex images from said subarrays to form an ultrasound image.

DRAWINGS

These and other features, aspects, and advantages of the present system and techniques will become better understood when the following detailed description is read with reference to the accompanying drawings in which like characters represent like parts throughout the drawings, wherein.

DETAILED DESCRIPTION

Figure 1:
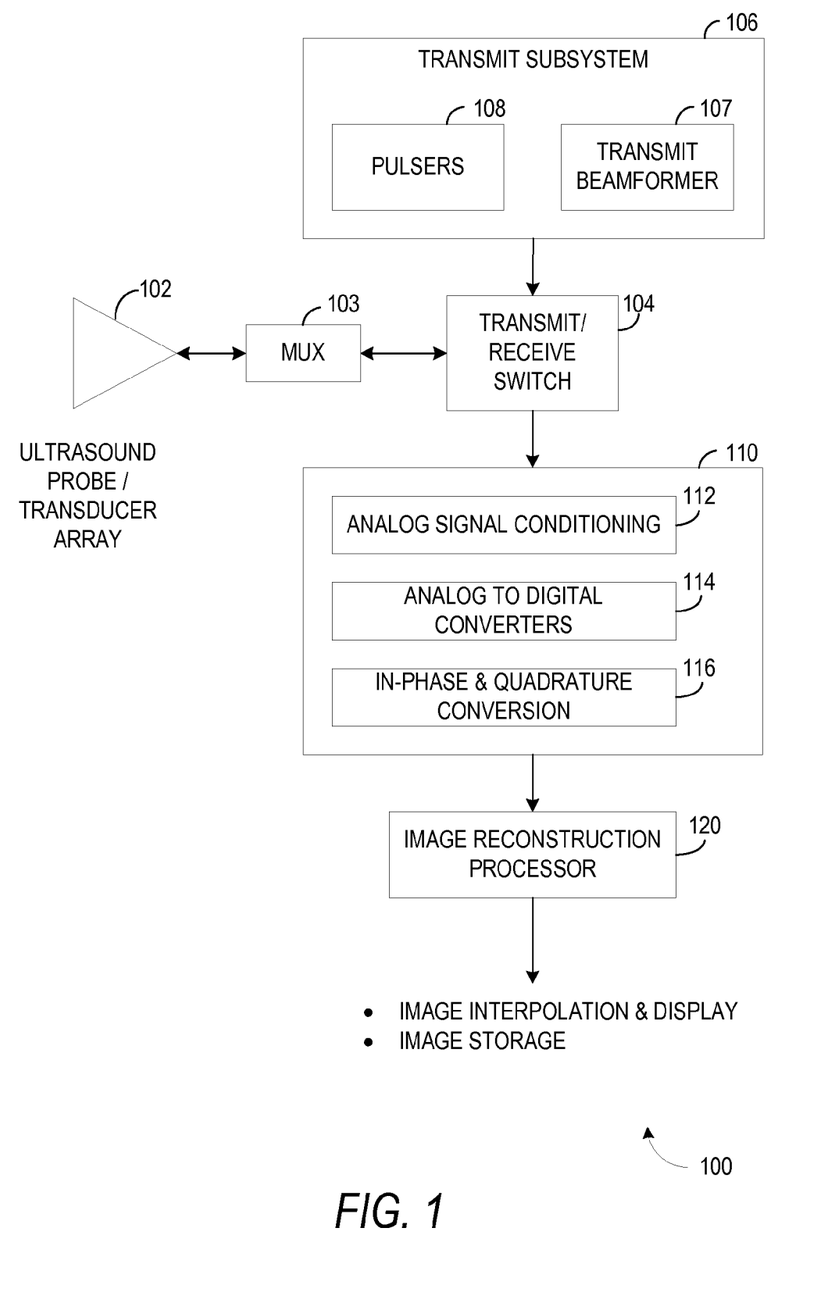
FIG. 1 is a block diagram of an example ultrasound imaging system, according to one embodiment.
Figure 3:
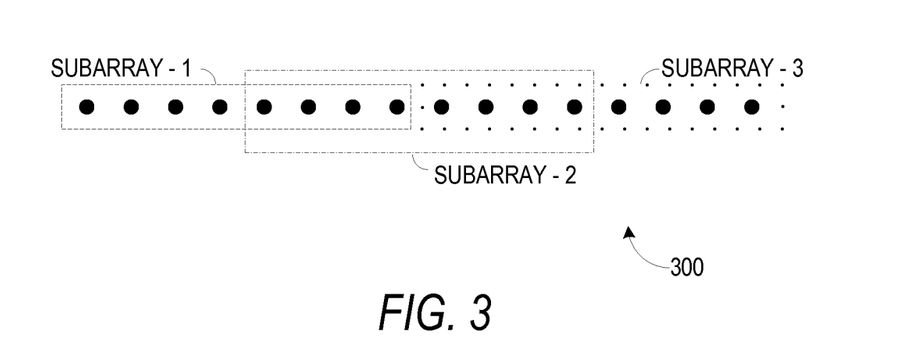
FIG. 3 is a schematic illustrating an example configuration of subarrays, according to one embodiment

FIG. 1 is a simplified block diagram of an example ultrasound imaging system 100. The ultrasound imaging system 100 in this example includes a transducer array 102, a multiplexor 103, a transmit/receive switch 104, a transmit subsystem 106, a received signal processing section 110 and an image reconstruction processor 120. The signal processing section in this example includes an analog signal conditioning unit 112 and a digitization block 114 that optionally performs In-phase and Quadrature conversion 116 on the sampled RF signals, The transducer array 102 includes a plurality of transducer elements. In one example the transducer array may typically include, for example, between 8 and 32 transducer elements. The multiplexor 103 in one example is used to define one or more subarrays of multiple transducer elements for transmission. The subarrays may be overlapping, where two or more subarrays may include a number of common transducer elements. Alternatively, the subarrays may be non-overlapping, where no two subarrays include any common transducer elements. Further, the subarrays may include contiguous transducer elements, or non-contiguous transducer elements, for example, alternate transducer elements. One example configuration of subarrays is illustrated in FIG. 3. The transducer elements typically serve as transmit elements as well as receive elements.

The transmit/receive switch 104 in this embodiment switches the transducer array 102 between a transmit mode and a receive mode. The transmit/receive switch 104 may include a crosspoint switch to protect components in the receiver section from high voltage pulses transmitted by the transmit processor 106. In one example, a separate analog switch is provided for each physical array element.

In the transmit mode, the transmit/receive switch 104 couples the transducer array 102 to the transmit subsystem 106. The transmit subsystem 106 includes the transmit beamformer 107 and the transmit pulser 108. The transmit beamformer 107 computes a transmit delay structure that enables directional transmission of a beam of ultrasound pulses. The transmit beamformer 107 generates a control sequence for timing the emission of ultrasound pulses from the transducer elements, to emit a directional beam of ultrasound signals. As used herein, "ultrasound beam" refers to a spatially directed pulse of ultrasound energy. In various embodiments, the transmit beamformer 107 may control some or all of the subarrays individually. In other words, the transmit beamformer 107 in one example causes the subarrays to transmit distinct beams of ultrasound energy, at preset beamsteering angles, using only the transducer elements of that subarray.

The control sequence triggers the transmit pulser 108 to generate high voltage pulses according to the control sequence of the transmit beamformer 107. The transmit pulser 108 then applies the high voltage pulses to the appropriate transducer element through the transmit/receive switch 104 and the multiplexor 103, based on the control sequence generated by the transmit beamformer 107 and the selected transmit subarray. The transmit pulser 108 in one example controls the amplitude of the electrical pulses to change the intensity and energy of the transmitted beam of ultrasound pulses.

Thus, a spatially directional beam of ultrasound pulses is transmitted from the subarrays of the transducer array 102. The spatially directional beams insonify a particular point in the area to be imaged. The transmit beamformer 107 insonifies the complete area to be imaged by generating different control sequences for transmitting multiple beams of ultrasound pulses. In one example, each of the beams originating from a given subarray is directed in a different direction.

In a typical operation, upon completing transmission of one beam of ultrasound pulses, the transmit/receive switch 104 switches from the transmit mode to the receive mode. In the receive mode, the transmit/receive switch 104 couples the transducer array 102 to the received signal processing section 110. In one example, the analog signal conditioning circuitry 112 includes circuits such as low noise amplifiers, voltage controlled amplifiers, and programmable gain amplifiers to condition the received ultrasound signals for processing. One such signal exists for each element of the array, and in one exemplary system, all such signals are used for reconstruction, while in another exemplary system, only a subset of these signals is used. The conditioned ultrasound signals from the analog signal conditioning section 112 are then processed by the signal digitization module 114.

The signal digitization module 114 takes the analog signals derived from the receive elements and converts them to a digital representation using analog-to-digital converters. In one example, system the sample rate required for such an operation will be approximately 50 MHz. Optionally, the system converts the sampled RF signals to In-phase and Quadrature (I/Q) representation of the ultrasound reflection using an In-phase and Quadrature unit 116. This is especially advantageous if the signals are transferred across a limited bandwidth bus prior to being stored in a memory such as a random access memory. In one example, the sample rate required for the complex-valued I/Q data will be approximately 10 MHz. The data set resulting from the analog-to-digital conversion is called the measured element data, because there is one set of digitized samples for each element in the array.

In one embodiment the output of the received signal processing section 110 is a set of measured element data residing in random access memory. The measured element data is then accessed by an image reconstruction processor 120. In one embodiment, the image reconstruction processor 120 may implement an operation equivalent to a delay-and-sum type beamformer. The image reconstruction processor 120 accepts a plurality of input signals, corresponding to the ultrasound transducer elements. In one example the image reconstruction processor 120 applies a delay to each of the input signals and computes a sum of the delayed input signals, to obtain a beam sum of the input signals corresponding to a particular point in space to the imaged. The image reconstruction processor 120 may be implemented as a hardware module or as a software procedure executed on a general-purpose or special-purpose processor.

Further, the image reconstruction processor 120 may be configured to select one set of ultrasound measurement data for each point to be imaged, corresponding to each of the one or more subarrays used to transmit. The image reconstruction processor 120 in one example selects the set of ultrasound measurements corresponding to the transmitted ultrasound beam having a beamsteering angle closest to the angle of a line segment joining the center of the subarray to the point to be imaged. According to one embodiment the image reconstruction processor 120 may first identify coordinates of the point to be imaged, and compute a pixel angle. The pixel angle may be defined as the angle between a normal to the subarray and a line joining the point to be imaged and a physical center of the subarray. The image reconstruction processor 120 may then select the ultrasound element data based on the pixel angle, the beamsteering angle of the corresponding transmitted ultrasound beam, and a pre-computed beam width of the ultrasound beam. The image reconstruction processor 120 in one example considers only the selected ultrasound element data sets for reconstructing an ultrasound image. Such a reconstruction step may be performed once for every subarray and the result coherently added together. By coherent addition, we mean phase-sensitive addition of signals. This is in contrast to the TFM method, in which this step is performed once for every array element. Thus, the present approach represents a significant reduction in the computational requirement, compared to the TFM approach. After coherent addition of the signals, the envelope of the sum signal is computed.

The image reconstruction processor 120 may optionally be connected to a scan converter. The scan converter interpolates an ultrasound image on a pre-determined rectilinear sample grid based on the reconstructed image points produced from the set of ultrasound measurements. The scan converter converts the reconstructed image samples into a digital image matrix format compatible with a display. If the reconstructed data is in the R-theta (i.e. polar coordinates) format used in standard ultrasound imaging, then the scan converter implements a transformation into X-Z coordinates (i.e. Cartesian coordinates), along with an interpolation operation. If the reconstructed samples are in a uniform X-Z sampling scheme, then only the imaging interpolation step need be performed. The scan converter may also perform other image processing related functions such as contrast and brightness control.

The display comprises a screen such as, but not limited to an LCD panel, a TFT, an electrophoretic display, and the like. The display provides a visual representation of the ultrasound image. The display may support color or grey scale representation of the ultrasound image.

The image reconstruction processor 120 may also be connected to an image storage or transmission device, such as a hard disk or random access memory, for retention of a sequence of images. The image reconstruction processor 120 in one example is coupled to a communications mechanism to transmit the images elsewhere.

Figure 2A:
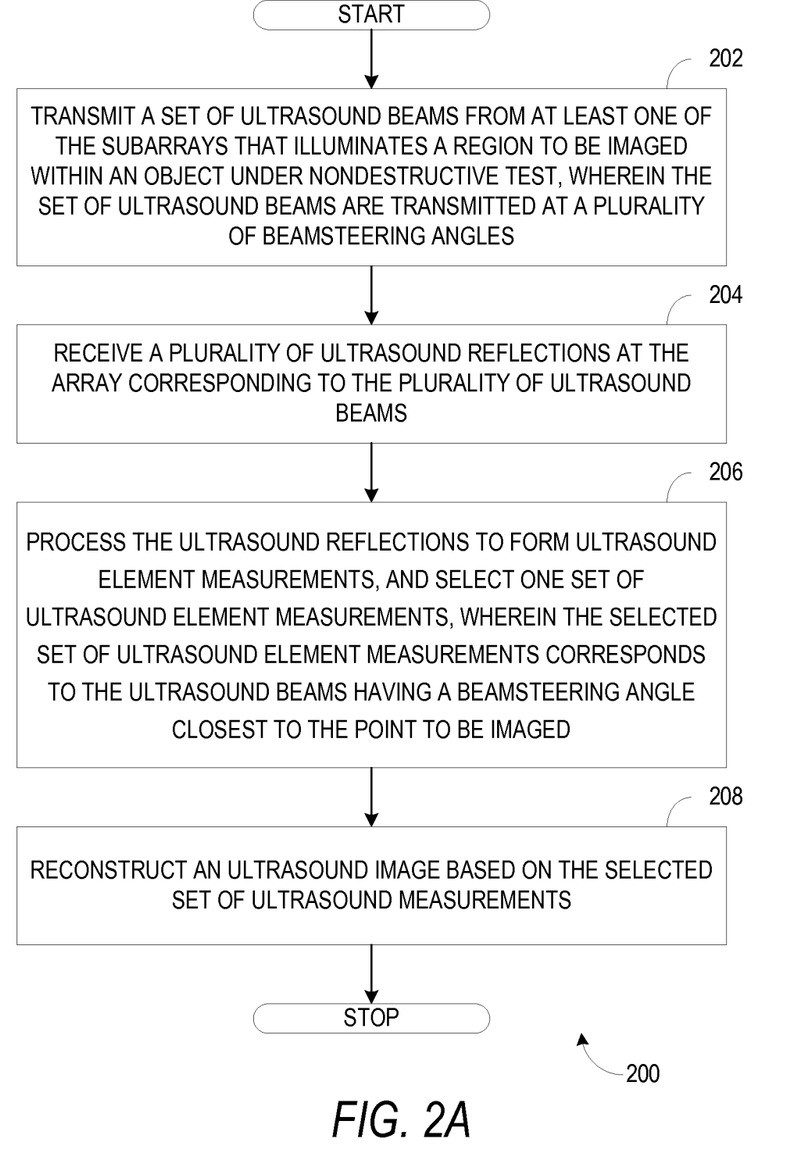
FIG. 2*a* is a flowchart illustrating an example process for ultrasound imaging, according to one embodiment.

FIG. 2a illustrates an example process for ultrasound imaging, according to one embodiment. Prior to executing the process for ultrasound imaging, the ultrasound imaging system 100 may first define one or more subarrays, such that each of the subarrays includes a plurality of ultrasound transducer elements. The subarrays may be overlapping, where two or more subarrays may include a number of common transducer elements. Alternatively, the subarrays may be non-overlapping, where no two subarrays include any common transducer elements. Further, the subarrays may include contiguous transducer elements, or non-contiguous transducer elements, for example, alternate transducer elements.

FIG. 3 illustrates one example subarray arrangement 300 comprising three subarrays, wherein each of the subarrays comprises eight ultrasound transducer elements. The subarrays are labeled as subarray-1, subarray-2 and subarray-3 as shown in the figure. Moreover, the ultrasound transducer elements of subarray-1 and subarray-3 have distinct ultrasound transducer elements, while that of subarray-2 overlap with the ultrasound transducer elements of subarray-1 and subarray-3.

In one embodiment, the number of ultrasound transducer elements in the one or more subarrays may be fixed. In another embodiment, the number of ultrasound transducer elements present in the one or more subarrays may be reconfigurable. The example subarray arrangement depicted herein is merely on an illustrative basis. A variety of similar such subarray arrangements may be configured without deviating from the scope of the system. In one example, the reconfigurable subarray arrangement can employ a plurality of transducer elements wherein a subset of the transducer elements in the individual subarray are employed for a particular ultrasound imaging sequence.

At step 202, a set of ultrasound beams is transmitted from each of the plurality of subarrays into the object under test. The set of ultrasound beams includes a plurality of ultrasound beams transmitted in one example at a corresponding plurality of beamsteering angles. In non-destructive testing of stationary objects, a single set of ultrasound beams with a single beam in each beamsteering direction provides sufficient data for image reconstruction, since motion artifacts due to the object moving between successive transmissions of the ultrasound signals may not occur. Since the one or more subarrays include multiple ultrasound transducer elements, the subarrays provide better penetration than a single transducer element by imparting more energy. Further, the subarrays are more directional than the single transducer elements.

The beamsteering angles may be determined based on the number of elements in the subarray, and the spacing between successive elements of the subarray. Thus, in the example illustrated in FIG. 3, thirteen ultrasound beams may be transmitted from each of the three subarrays at beamsteering angles ranging from −48 degrees to +48 degrees, incrementing in steps of 8 degrees. Further, the transmitted ultrasound signals may be focused at a fixed focal distance, for instance 10 cm. Those skilled in the art will readily appreciate that a variety of other factors, such as aperture width, beam width, and the like may also be considered while computing the appropriate beamsteering angle to cover the entire area to be imaged.

The angle between beams in one example is designed to be as large as possible, consistent with the goal of illuminating the entire scene to be imaged. By reducing the number of transmits required to form an image, the bus capacity required for data transfer between the signal digitization module and the image reconstruction processor may be minimized, without compromising on uniform focus throughout the ultrasound image. This is especially important in a software-based system, in which the receive beamformer is not a hardware module. For example, consider a case to synthesize a scan composed of 81 fully-focused A-lines using three subarrays. According to the conventional STA method this would typically require 243 sets of receive element data. In contrast, the exemplary process described herein allows as few as nine transmits per 8-element subarray. This would require 27 sets of receive element data to form a substantially equivalent image. However, this decrease in the number of transmissions is generally only accomplished if any set of transmissions can be coherently combined, which is only the case if there is no motion in the scene to be imaged. It is often the case in nondestructive testing that the scene to be imaged is not in motion.

At step 204, the ultrasound transducer elements of the transducer array receive a plurality of ultrasound reflections corresponding to the plurality of ultrasound beams.

At step 206, these signals are digitized and so converted into ultrasound element measurement data. For the one or more subarrays, one set of ultrasound measurements for each point to be imaged is selected. In one embodiment, the selected set of ultrasound element measurements corresponds to an ultrasound beam having a beamsteering angle closest to the angle of the point to be imaged. The selection of the set of ultrasound element measurements to be used in reconstruction may be performed so as to select the ultrasound measurements corresponding to the ultrasound beam that delivers the most energy to the point to be imaged.

According to one embodiment, an exemplary process to select the one set of ultrasound element measurements per subarray for use in image reconstruction is described hereinafter. The exemplary process involves identifying coordinates of the point to be imaged. Next, a pixel angle is computed based on the identified coordinates. The pixel angle is defined as the angle between a normal to the subarray and a line joining the point to be imaged and a center of the subarray. Finally, one ultrasound beam per subarray is identified based upon factors including, but not limited to, the pixel angle, the beamsteering angle of the corresponding ultrasound signal, the beam width of the ultrasound signal, and the like. Other known algorithms may also be used in the selection of the ultrasound reflection, such that the selected ultrasound reflection per subarray has a focal point closest to the point to be imaged.

Subsequently at step 208, a sample of the ultrasound image is reconstructed. Each sample may represent a single point in the object under test. The sample is reconstructed based on the selected ultrasound element data obtained at step 204. In one embodiment, using the well-known In-phase and Quadrature (I/Q) representation of the signal, the reconstruction of the ultrasound image is based on an example equation defined as:

$$I(x,y) = \left| \sum_{s=1}^{SA} \sum_{t \in T_s} \sum_{n=1}^{N} (I_{n,t}(D_n(x,y) + D_{0,s}(x_{s,t}, y_{s,t}) - \Delta(x,y,x_{s,t},y_{s,t})) + jQ_{n,t}(D_n(x,y) + D_{0,s}(x_{s,t}, y_{s,t}) - \Delta(x,y,x_{s,t},y_{s,t})))e^{j2\pi f_0 \tau_0} \right|^2 \quad \text{Equation 1}$$

where s is an index identifying a subarray, SA is the number of subarrays, t is an index identifying one of a set of fixed focus transmissions performed by subarray 's', $T_s$ is the set of indices of transmissions performed by subarray 's' that is to be used in the reconstruction of the point (x,y), ($x_{s,t}$, $y_{s,t}$) are the coordinates of the of the transmit focus of the subarray 's' for fixed-focus transmission number 't', (x, y) are the coordinates of a point to be imaged, N is the number of elements in the receive array, $I_{n,t}$ represents the in-phase component of the ultrasound measurement data for receive element 'n' for transmit number 't', and $Q_{n,t}$ represents the quadrature component of the ultrasound measurement data for receive element 'n' for transmit number 't', $f_0$ is the center frequency of the ultrasound, $\tau_n$ is the propagation time from the $n^{th}$ array element to the point to be reconstructed minus the minimum such propagation time over all the elements in the array, $D_{0,s}(x_{s,t}, y_{s,t})$ represents the delay from the phase center of the subarray with index 's' to the focal point ($x_{s,t}$, $y_{s,t}$) of the $t^{th}$ transmission from subarray 's', $D_n(x,y)$ represents the delay from element n to the point (x,y), and $\Delta(x,y,x_{s,t},y_{s,t})$ represents the propagation delay that would be associated with propagation over the linear distance between the point ($x_{s,t}$, $y_{s,t}$) and the point (x,y).

In the example Equation 1 given above the one or more selected ultrasound element signal sets are considered for reconstruction. In case the set $T_s$ has only one element, the point ($x_{s,t}$, $y_{s,t}$) represents the coordinates of the focal point which lies closest to the point to be imaged (x, y). In one embodiment, the index 't' of the point ($x_{s,t}$, $y_{s,t}$) may be determined by the example process as described earlier.

Each of the samples reconstructed individually may then be stored such as into an output image buffer, for complete ultrasound image formation. Based on the reconstructed samples, at step 210, the ultrasound image is formed. For example, the reconstructed samples may be tiled or arranged in a two dimensional space to form the ultrasound image. Any known tile alignment and placement algorithm may be used to form the ultrasound image from the individual reconstructed samples.

Figure 2B:
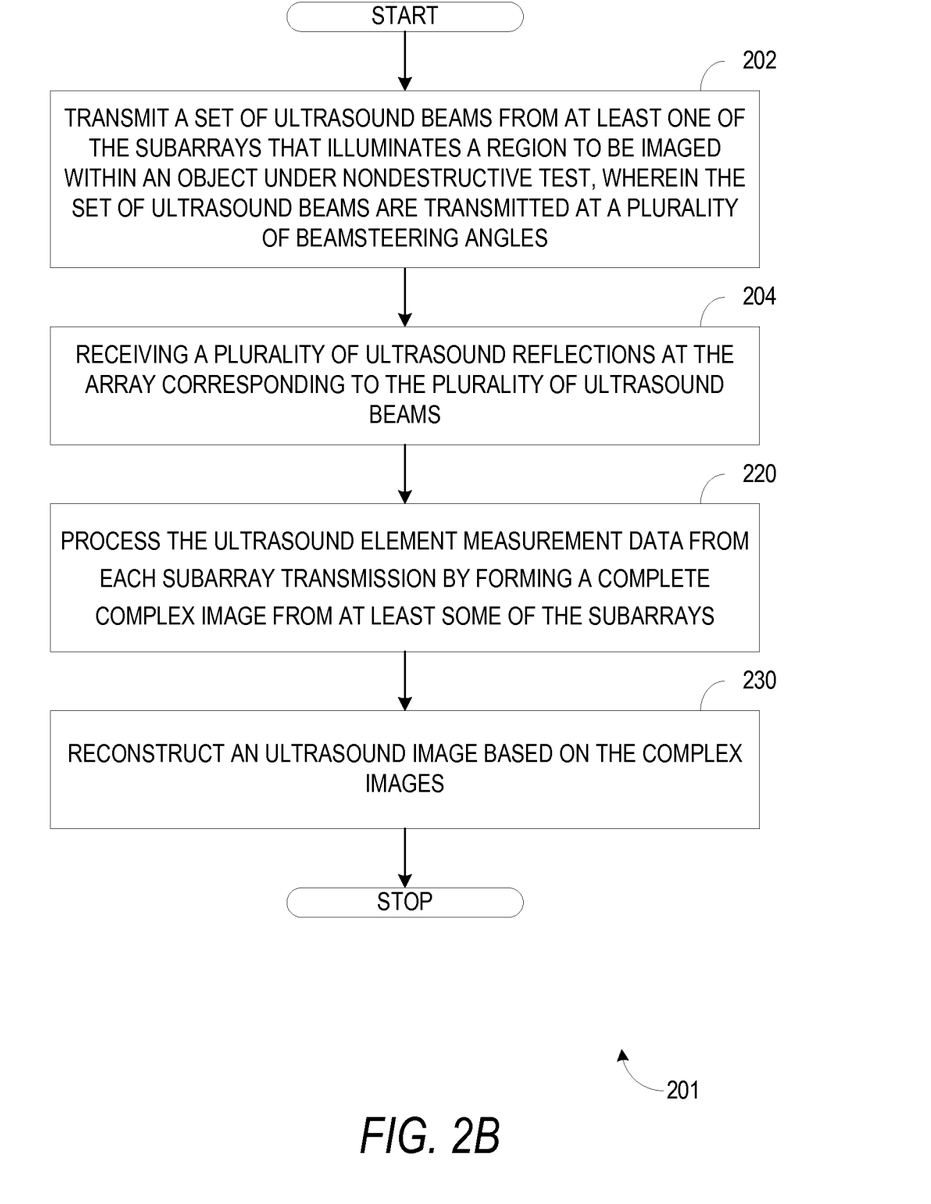
FIG. 2*b* is a flowchart illustrating another example process for ultrasound imaging, according to one embodiment.

An alternative mode of image reconstruction is also accommodated by the system detailed herein and shown in FIG. 2b. As previously noted, at step 202, ultrasound beams are transmitted from each of the plurality of subarrays into the object under test, and at step 204 the ultrasound transducer elements of the transducer array receive and measure a plurality of ultrasound reflections corresponding to the plurality of ultrasound beams. Instead of image reconstruction as noted in FIG. 2a, wherein each sample of the image is computed independently and the results stored such as into an output image buffer at step 220, the alternative mode of image reconstruction is processed such that each subarray is used to form a complete complex image which is stored, for example in a RAM buffer. Each of the complex images represent the image captured by the entire array in response to a set of transmissions from a single subarray that illuminate the entire scene to be imaged. Each pixel is obtained from that beam which has beam steering angle closest to the pixel angle. At step 230, the complex images from each subarray transmission may then be combined such as being added together. The combining of the images may be followed by further reconstruction processing, such as by computing the squared modulus of the sum. This approach has the advantage of allowing for a more regular pattern for accessing the measured element data. It also allows some interleaving of data gathering and computation, since the first subarray's data could be used to form the first complex subimage while the second subarray's data was still being acquired.

In terms of Equation 1, the alternative method consists of forming SA complex-valued component images using the formula $$I_s(x,y) = \sum_{t \in T_s} \sum_{n=1}^{N} (I_{n,t}(D_n(x,y) + D_{0,s}(x_{s,t}, y_{s,t}) - \Delta(x,y,x_{s,t},y_{s,t})) + jQ_{n,t}(D_n(x,y) + D_{0,s}(x_{s,t}, y_{s,t}) - \Delta(x,y,x_{s,t},y_{s,t})))e^{j2\pi f_0 \tau_0} \quad \text{Equation 2}$$

The component images are then summed for s=1, . . . , SA, and the modulus of the result is taken. This is the same operation as is given by Equation 1, with intermediate data storage used to store each complex-valued component image.

FIG. 3 referred to earlier, is a schematic illustrating an example configuration of subarrays. The arrangement depicted in the figure comprises overlapping subarrays, namely subarray-1 and subarray-3, and overlapping subarray-2. A person of ordinary skill in the art will appreciate that the overlapped subarray arrangement provides effective transmit apodization to each reconstruction, which assists in sidelobe reduction, because the elements near the center of the array are used for transmission twice as often as the elements near the edges of the array. Additionally, the arrangement depicted herein is merely on an illustrative basis and does not limit the scope of the invention.

The present system according to one example finds applicability in portable nondestructive evaluation systems, typically where the reflectivity distributions are typically not in motion.

Figure 4A:
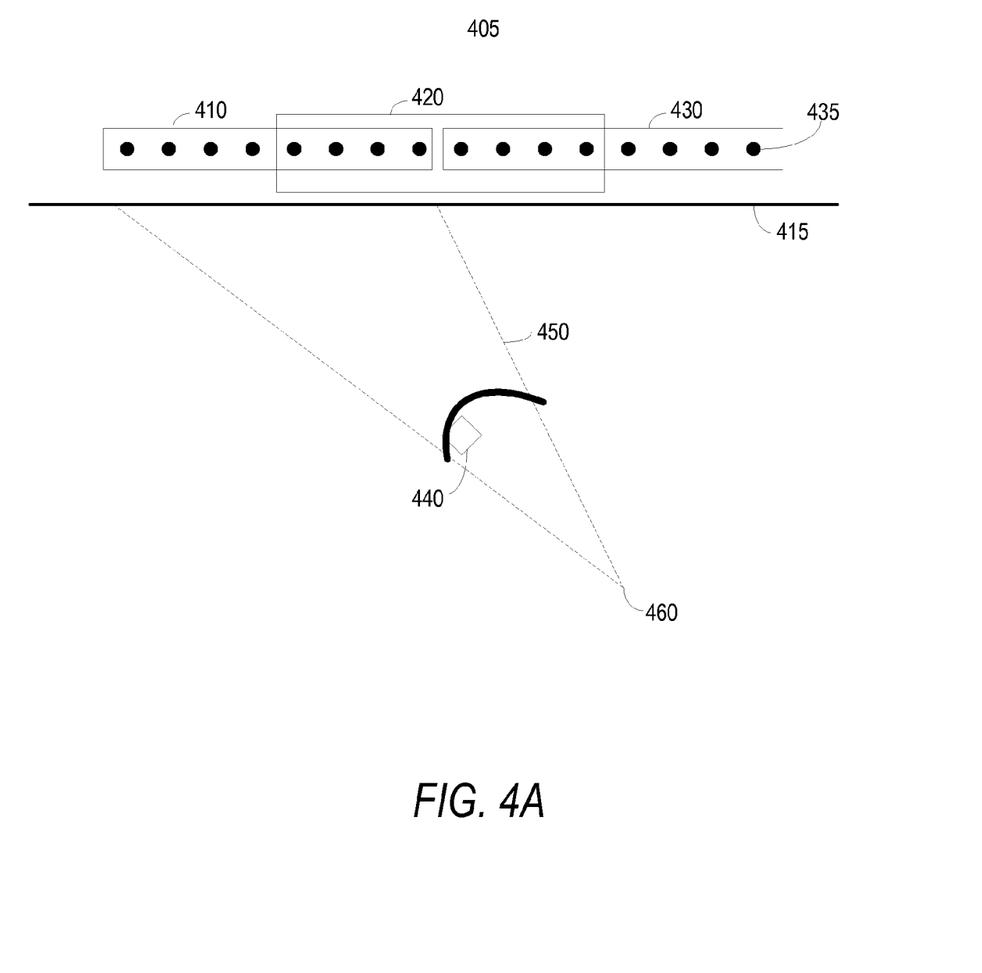
FIG. 4*a-c* illustrates one illustrative embodiment for ultrasound imaging.
Figure 4B:
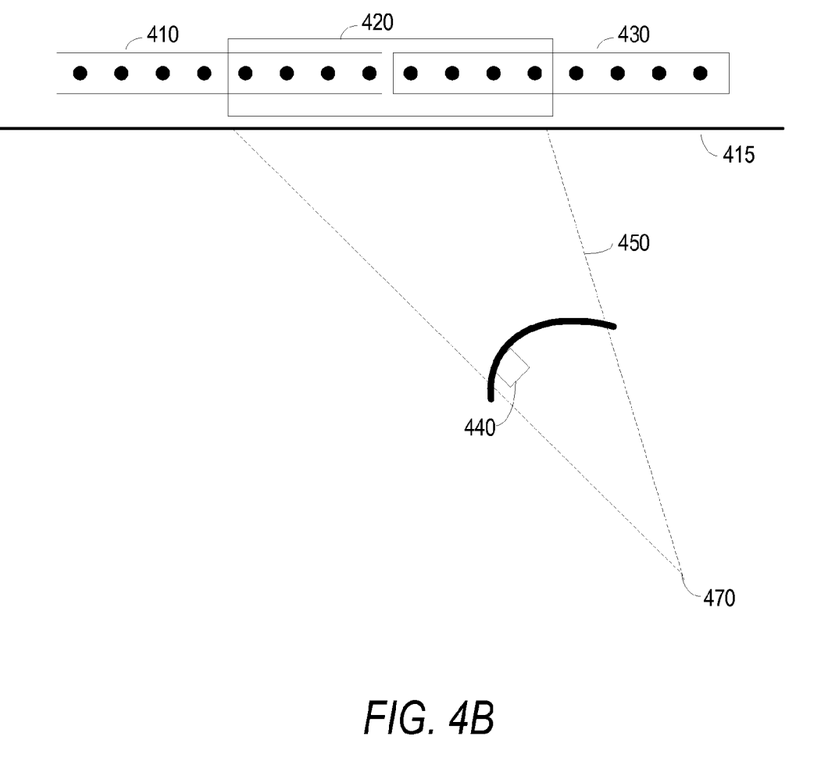
Figure 4C:
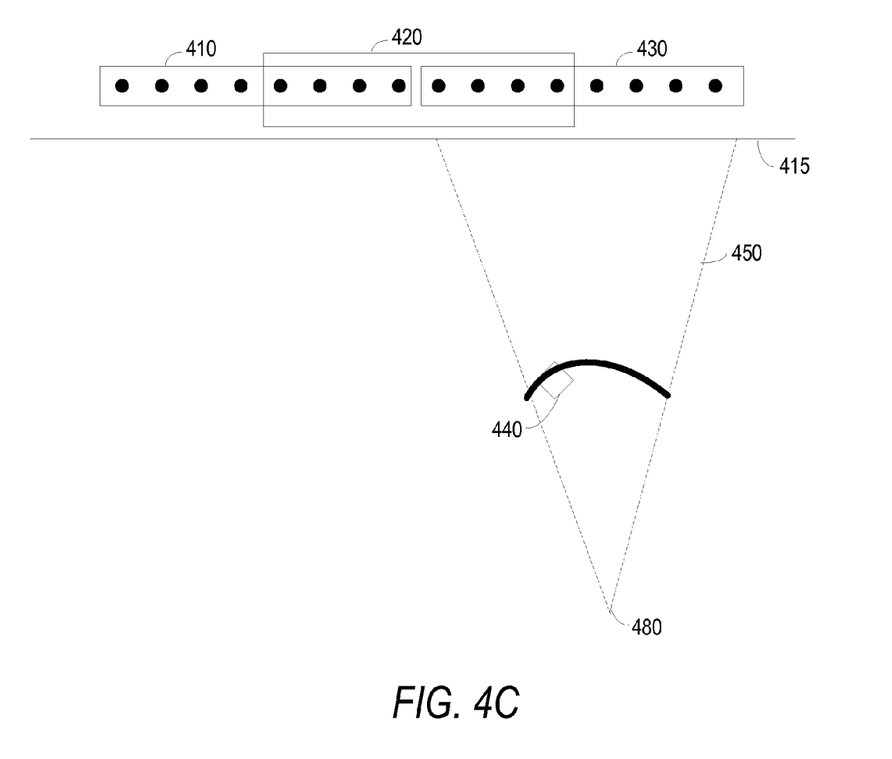

Referring to FIG. 4a-4c, an ultrasound imaging technique is pictorially represented. In FIG. 4a, there is an array of transducer elements 405 disposed upon or proximate a material surface 415. In this example the array 405 is divided into three subarrays 410, 420, 430. Each of the subarrays has a number of transducers 435, wherein in this example there are three overlapping subarrays 410, 420, 430 each having eight transducers. It is noted that the number of transducers 435 can be any practical number of transducers depending upon the application. In addition, the overlapping subarray can have an equal number of transducers 435 from adjacent subarrays or can have a greater number of transducers from one subarray.

FIG. 4a illustrates the processing for the first subarray which picks the transmit beam from the first subarray that illuminates the point to be imaged 440. The system focuses the transmit subarray on the chosen focal point of the first subarray 460. The converging acoustic wavefront 450 isonifies the point to be imaged. The received RF or I/Q data for this first subarray illumination is digitized and stored for each array element.

Referring to FIG. 4b, the transmit beam from the second subarray illuminates the point to be imaged. The transmit beam from the second subarray illuminates the point to be imaged 440 and the system focuses the transmit subarray on the chosen focal point of the second subarray 470. The converging acoustic wavefront 450 isonifies the point to be imaged. The received RF or I/Q data from the second subarray is digitized and stored for each array element.

As shown in FIG. 4c, the transmit beam from the third subarray illuminates the point to be imaged. The transmit beam from the third subarray illuminates the point to be imaged 440 and the system focuses the transmit subarray on the chosen focal point of the third subarray 480. The converging acoustic wavefront 450 isonifies the point to be imaged. The received RF or I/Q data from the third subarray is digitized and stored for each array element.

The data acquired from the process depicted in FIG. 4a-c is used to compute an image point, for example by using the formula given by Equation 1 in the case of I/Q data, in which the number of subarrays is three, the first set of data is indexed by s=1, the transmit beam index may be 3, so that $T_s=\{3\}$, corresponding to the third transmission from subarray 1 depicted schematically in FIG. 4a, and the receive data measurement is done at all the array elements, the second set of data is indexed by s=2, the transmit beam index may be 5, so that $T_s=\{5\}$, corresponding to the fifth transmission from subarray 2 depicted schematically in FIG. 4b, and the receive data measurement is done at all of the array elements, and the third set of data is indexed by s=3, the transmit beam index may be 7, so that $T_s=\{7\}$, corresponding to the seventh transmission from subarray 3 depicted schematically in FIG. 4c, and the receive data measurement is done at all of the array elements. Note that the transmissions need not be contiguous or have any other time relationship to each other, since the scene to be imaged is not in motion. Once the coherent addition of the signal data has been accomplished, the square of the signal envelope is derived by taking the squared modulus of the complex result.

The methods disclosed herein can be embodied in the form of computer or controller implemented processes and apparatuses for practicing these processes. These methods can also be embodied in the form of computer program code containing instructions embodied in tangible media, such as floppy diskettes, CD-ROMs, hard drives, and the like, wherein, when the computer program code is loaded into and executed by a computer or controller, the computer becomes an apparatus for practicing the method. The methods may also be embodied in the form of computer program code or signal, for example, whether stored in a storage medium, loaded into and/or executed by a computer or controller, or transmitted over some transmission medium, such as over electrical wiring or cabling, through fiber optics, or via electromagnetic radiation, wherein, when the computer program code is loaded into and executed by a computer, the computer becomes an apparatus for practicing the method. When implemented on a general-purpose microprocessor, the computer program code segments configure the microprocessor to create specific logic circuits.

While the invention has been described in considerable detail with reference to a few exemplary embodiments only, it will be appreciated that it is not intended to limit the invention to these embodiments only, since various modifications, omissions, additions and substitutions may be made to the disclosed embodiments without materially departing from the scope of the invention. In addition, many modifications may be made to adapt to a particular situation or an installation, without departing from the essential scope of the invention. Thus, it must be understood that the above invention has been described by way of illustration and not limitation. Accordingly, it is intended to cover all modifications, omissions, additions, substitutions or the like, which may be included within the scope and the spirit of the invention as defined by the claims.

The invention claimed is:

1. A method for ultrasound imaging, the method comprising:
    defining a plurality of subarrays of an array, wherein each of the plurality of subarrays comprises a plurality of ultrasound transducer elements;
    transmitting a set of ultrasound beams from at least one of the subarrays that illuminates a region to be imaged within an object under nondestructive test, wherein the set of ultrasound beams are transmitted at a plurality of beamsteering angles;
    receiving a plurality of ultrasound reflections at the array corresponding to the plurality of ultrasound beams;
    processing the ultrasound reflections and forming ultrasound element measurements, and selecting one set of ultrasound element measurements for a point to be imaged based on a beamsteering angle of the corresponding ultrasound beams, wherein the selected set of ultrasound element measurements corresponds to the ultrasound beams having a beamsteering angle closest to an angle from the array to the point to be imaged;
    reconstructing a sample of an ultrasound image of the object under nondestructive test based on the selected set of ultrasound element measurements; and
    reconstructing a plurality of such samples to form an ultrasound image.

2. The method of claim 1, wherein the plurality of subarrays comprises one or more ultrasound transducer elements that are common to at least one other subarray.

3. The method of claim 1, wherein the plurality of subarrays comprises distinct ultrasound transducer elements.

4. The method of claim 1, wherein the plurality of beamsteering angles are preset beamsteering angles based on a number of ultrasound transducer elements in the plurality of subarrays.

5. The method of claim 1, wherein the plurality of ultrasound beams is focused at a predefined focal distance.

6. The method of claim 1 wherein selecting the ultrasound element measurements comprises:
    identifying coordinates of the point to be imaged;
    computing a pixel angle as the angle between a normal to the subarray and a line joining the point to be imaged and a center of the subarray, based on the identified coordinates; and identifying an ultrasound reflection based on the pixel angle, the beamsteering angle of a corresponding ultrasound beam, and a beam width of the ultrasound beam.

7. A system for ultrasound imaging, the system comprising:
   an ultrasound transducer array divided into a plurality of subarrays, wherein each of the plurality of subarrays comprises a plurality of ultrasound transducer elements;
   a transmit beamformer configured to transmit a set of ultrasound beams from each of the plurality of subarrays into an object under nondestructive test, wherein the set comprises a plurality of ultrasound beams transmitted at a plurality of beamsteering angles;
   a received signal processor for receiving a plurality of ultrasound reflections and converting each of the ultrasound reflections into a measured ultrasound element data, wherein each of the plurality of ultrasound reflections correspond to one of the plurality of transmitted ultrasound beams;
   a receive beamformer configured to select one set of measured ultrasound element data for each point to be imaged based on a beamsteering angle of the corresponding ultrasound beams, from each of the plurality of subarrays, wherein the selected set of measured ultrasound element data corresponds to the ultrasound beams having a beamsteering angle closest to an angle from the array to the point to be imaged; and
   an image reconstruction processor for reconstructing an ultrasound image of the object under nondestructive test based on the selected set of measured ultrasound element data.

8. The system of claim 7, wherein the plurality of subarrays comprises one or more ultrasound transducer elements that are common to at least one other subarray.

9. The system of claim 7, wherein the plurality of subarrays comprises distinct ultrasound transducer elements.

10. The system of claim 7, wherein the plurality of beamsteering angles are preset beamsteering angle based on a number of ultrasound transducer elements in each of the plurality of subarrays.

11. The system of claim 7, wherein the plurality of ultrasound beams is focused at a predefined focal distance.

12. The system of claim 7 wherein the receive beamformer is further configured to
   identify coordinates of the point to be imaged, and compute a pixel angle as the angle between a normal to the subarray and a line joining the point to be imaged and a center of the subarray, based on the identified coordinates; and
   identify an ultrasound reflection based on the pixel angle, the beamsteering angle of a corresponding ultrasound beam, and a beam width of the ultrasound beam.

13. The system of claim 7, wherein the image reconstruction processor is a scan convertor.

14. A computer program product comprising a non-transitory computer readable medium encoded with computer-executable instructions, wherein the computer-executable instructions, when executed, cause one or more processors to:
   define a plurality of subarrays of a transducer array, wherein each of the plurality of subarrays comprises a plurality of ultrasound transducer elements;
   transmit a set of ultrasound beams from at least one of the plurality of subarrays into an object under nondestructive test, wherein the set comprises a plurality of ultrasound beams transmitted at a plurality of beamsteering angles;
   receive, at the transducer array, a plurality of ultrasound reflections corresponding to the plurality of ultrasound beams;
   for the plurality of subarrays, process the ultrasound reflections to form ultrasound element measurements and select ultrasound element measurements for a point to be imaged based on a beamsteering angle of the corresponding ultrasound beams, wherein the selected set of ultrasound element measurements corresponds to ultrasound beams having a beamsteering angle closest to an angle from the array to the point to be imaged;
   reconstruct a sample of the ultrasound image of the object under test based on the selected ultrasound reflections; and
   reconstructing a plurality of such samples to form an ultrasound image.

15. The computer program product of claim 14, wherein the plurality of subarrays comprises one or more ultrasound transducer elements that are common to at least one other subarray.

16. The computer program product of claim 14, wherein the plurality of subarrays comprises distinct ultrasound transducer elements.

17. The computer program product of claim 14, wherein the plurality of beamsteering angles are preset beamsteering angle based on a number of ultrasound transducer elements in each of the plurality of subarrays.

18. The computer program product of claim 14, wherein the plurality of ultrasound beams is focused at a predefined focal distance.

19. The computer program product of claim 14, further comprising computer executable instructions to cause the one or more processors to:
   identify coordinates of the point to be imaged;
   compute a pixel angle as the angle between a normal to the subarray and a line joining the point to be imaged and a center of the subarray, based on the identified coordinates; and
   identify an ultrasound reflection based on the pixel angle, the beamsteering angle of a corresponding ultrasound beam, and a beam width of the ultrasound beam.

20. A method for ultrasound imaging, the method comprising:
   defining a plurality of subarrays of an array, wherein each of the plurality of subarrays comprises a plurality of ultrasound transducer elements;
   transmitting a set of ultrasound beams from at least one of the subarrays that illuminates a region to be imaged within an object under nondestructive test, wherein the set of ultrasound beams are transmitted at a plurality of beamsteering angles;
   receiving a plurality of ultrasound reflections at the array corresponding to the plurality of ultrasound beams;
   processing the ultrasound element measurement data from each subarray transmission by forming a complete complex image from at least some of the subarrays, wherein the processing includes selecting one set of ultrasound element measurements for a point to be imaged based on a beamsteering angle of the corresponding ultrasound beams, wherein the selected set of ultrasound element measurements corresponds to the ultrasound beams having a beamsteering angle closest to an angle from the array to the point to be imaged;

reconstructing a sample of an ultrasound image of the object under nondestructive test based on the selected set of ultrasound element measurements; and reconstructing the complex images to form an ultrasound image.

21. The method of claim 20, wherein the plurality of subarrays comprises one or more ultrasound transducer elements that are common to at least one other subarray.

22. The method of claim 20, wherein the plurality of subarrays comprises distinct ultrasound transducer elements.

23. The method of claim 20, wherein the plurality of beamsteering angles are preset beamsteering angles based on a number of ultrasound transducer elements in the plurality of subarrays.

24. The method of claim 20, wherein the plurality of ultrasound beams is focused at a predefined focal distance.

* * * * *